United States Patent [19]

Hess et al.

[11] Patent Number: 5,076,285
[45] Date of Patent: Dec. 31, 1991

[54] SCREW-IN LEAD

[75] Inventors: Douglas N. Hess, Maple Grove; Kenneth R. Brennen, Fridley; Wayne R. Bass, Coon Rapids, all of Minn.

[73] Assignee: Medtronic, Inc., Minneapolis, Minn.

[21] Appl. No.: 502,605

[22] Filed: Mar. 30, 1990

[51] Int. Cl.$^5$ .............................................. A61N 1/05
[52] U.S. Cl. ................................... 128/186; 128/785; 128/419
[58] Field of Search .................... 128/419 P, 783, 784, 128/785, 786

[56] References Cited

U.S. PATENT DOCUMENTS

| | | | |
|---|---|---|---|
| 4,046,151 | 9/1977 | Rose | 128/785 |
| 4,106,512 | 8/1978 | Bisping | 128/418 |
| 4,146,036 | 3/1979 | Dutcher et al. | 128/418 |
| 4,381,013 | 4/1983 | Dutcher | 128/419 P |
| 4,570,642 | 2/1986 | Kane et al. | 128/785 |
| 4,967,766 | 11/1990 | Bradshaw | 128/785 |

OTHER PUBLICATIONS

Medtronic ® Model 6954 Transvenous Screw-In Ventricular Lead, Sep. 1977, Medtronic ® Transvenous Screw-In Ventricular Lead-Model 6954 Physician Manual for Product Performance Verification Study, Copyright ® 1976.
Medtronic ® Spectraflex Transvenous, Screw-In Ventricular Lead Model 6959.
Medtronic ® Transvenous, Unipolar, Screw-In Lead Moel 6957.

Primary Examiner—William E. Kamm
Assistant Examiner—Scott M. Getzow

[57] ABSTRACT

A cardiac pacing lead for endocardial use, having a pacing electrode which takes the form of a tapered, conical helix extending from the distal end of the lead. The helix is used to attach the distal end of the lead to heart tissues. The tapered shape of the helix facilitates passage of the lead through the venous system and through the tricuspid valve. Rotation of the fixation helix is accomplished by means of rotation of a coiled conductor extending the length of the lead, in conjunction with rotation of a stylet, passing down the conductor. The stylet is fixedly mounted with respect to the coiled conductor at both the proximal and distal ends of the lead.

7 Claims, 2 Drawing Sheets

SCREW-IN LEAD

BACKGROUND OF THE INVENTION

This invention relates to medical electrical leads in general, and to endocardial screw-in pacing leads, in particular.

In an effort to assure the stable location of an endocardial pacing electrode, a variety of approaches have been employed. One common approach is to employ an endocardial pacing lead which has a sharpened helix located at its distal end. This helix may either be the pacing electrode, or may be located adjacent the pacing electrode. The helix is rotated by some means from the proximal end of the lead and screwed into the endocardium, to permanently locate the electrode within the heart.

Within the general field of endocardial screw-in pacing leads, a number of different varieties have emerged. Early designs employed helixes that were fixedly mounted with respect to the end of the pacing lead, such as that disclosed in German Patent No. 2533766, 2539553, issued to Osypka. In this lead, rotation of the helix into the heart tissue was accomplished either by rotation of the entire lead, or by rotation of a stylet with a screwdriver tip, which engaged a slot located internal to the pacing lead, adjacent its distal end.

Later designs employed fixation helixes that were advanceable from or retractable into the distal end of the pacing lead to facilitate passage of the pacing lead through the venous system and through the tricuspid valve, one such lead is illustrated in U.S. Pat. No. 4,106,512 issued to Bisping. This patent discloses a lead in which the helix acts as the electrode, and is advanced out of the distal end of the lead by rotation of the coiled conductor within the lead body. An alternative approach to Bisping is illustrated in U.S. Pat. No. 4,217,913, issued to Dutcher. In this patent, a screwdriver tip stylet is employed to rotate the fixation helix out of the distal end of the lead. In this embodiment, the helix serves only to attach the lead to the tissue, and a separate ring electrode is supplied for stimulation purposes. In this lead, the stylet engages a slot within the distal end of the lead, located on a member which rotates with the fixation helix.

Yet another approach is illustrated in U.S. Pat. No. 4,570,642 issued to Kane et al. In this embodiment, the helix is located on a member which is slidable within the distal end of the pacing lead, and is advanced out of the distal end of the pacing lead by means of a cylindrical stylet which pushes a member located within the distal end of the lead, carrying the fixation helix. The fixation helix is screwed into the tissue by rotation of the entire lead.

Both the Kane and Dutcher leads disclose fixtures mountable on the connector pin of the pacing lead for facilitating employment of the helix. In the Dutcher lead, the fixture serves as a ratchet, allowing for advancement of the fixation helix out of the distal end of the lead. In Kane, the fixture stabilizes the longitudinal relationship of the stylet and pacing lead in order to hold the helix in an extended position.

SUMMARY OF THE INVENTION

The above three cited patents illustrate the alternative approaches that have been taken to providing a means for rotation of the helix into the heart tissue. Dutcher and Osypka both illustrate the use of a screwdriver shaped stylet to screw the helix into the tissue. Kane, Bisping and an alternative embodiment in Osypka illustrate the use of the helical conductor located within the lead body alone, or in conjunction with the lead body to provide rotational force to the tip of the lead.

Unfortunately, a stylet or the coiled conductor of a pacing lead does not efficiently transfer torque down the body of the pacing lead. As such, in most commercial screw-in pacing leads, the number of turns of the connector pin or the stylet at the proximal end of the lead does not precisely correspond to the number of rotations of the helix at the distal end of the lead.

The lead of the present invention addresses this problem in the context of a fixed helix type pacing lead by providing means for rotationally fixing a stylet located within the lead at both the proximal and distal ends of the lead. By this expedient, torque can be simultaneously transferred down the lead by both the stylet and the coiled conductor within the lead body.

In addition, the lead of the present invention attempts to address the problems of snagging of the helix as the lead is passed through the vein or through the tricuspid valve by provision of a unique helix configuration. The helix of the present lead is tapered, and employs a distal, sharpened point which intersects the central axis of the pacing lead. This configuration is believed to significantly reduce the chances of snagging or perforation of the lead as it is passed through the venous system and through the tricuspid valve area. Surprisingly, placing the sharpened tip of the helix on axis does not interfere with its ability to be screwed into heart tissue, as might otherwise be expected.

DETAILED DESCRIPTION OF THE DRAWINGS

Figure 1:
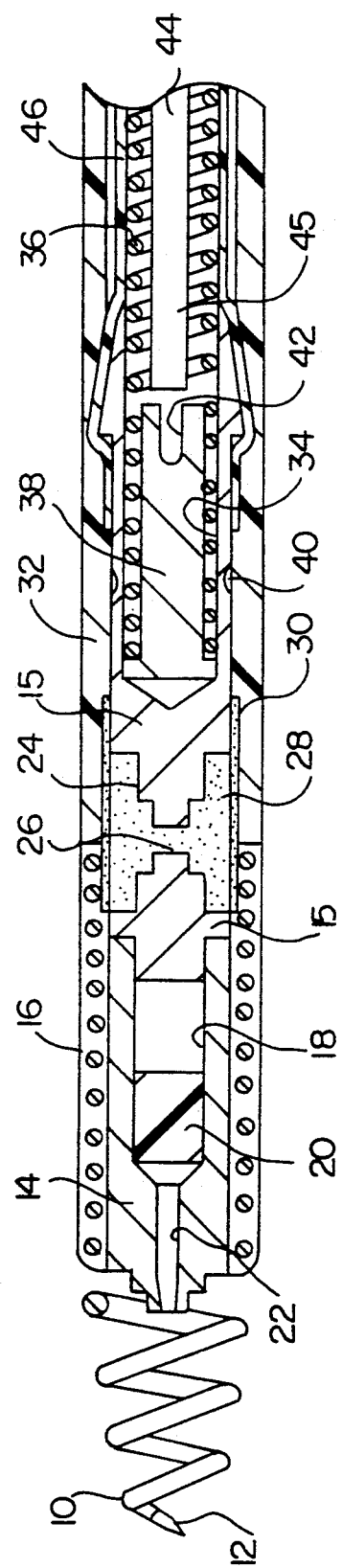
FIG. 1 is a side, cut away view of the distal end of a pacing lead according to the present invention.

FIG. 1 is a side, cut away view through the distal end of pacing lead according to the present invention. At the very distal end of the lead, a sharpened helix 10 is located, which extends distal to the distal portion of the lead body. Helix 10 is preferably conducted of an inert, biocompatible metal such as MP35N alloy, Elgiloy alloy, or a platinum alloy. As illustrated, helix 10 is generally a conical, tapered helix and the sharpened, distal end 12 of the helix is located intersecting the central axis of the lead. The lead is provided with an electrode head member 14, to which helix 10 is mounted by means of a plastic sleeve 16 in which the proximal end of helix 10 is embedded. Sleeve 16 may be fabricated of polyurethane or silicone rubber.

Located within head member 14 is an electrode chamber 18 which contains a monolithic controlled release device impregnated with a glucocorticosteroid, delivered to the distal end of the electrode head member 14 by means of a longitudinal bore 22, which may be filled with a porous, sintered structure to control elution rate of the steroid. Details of construction related to such electrodes are found in U.S. Pat. No. 4,506,680, issued to Stokes, incorporated herein by reference in its entirety. For the purpose of the present invention, it is only important that an electrode of some sort be included in the pacing lead. In some cases, the helix 10 may serve as the electrode.

Electrode head member 15 forms the proximal portion of the electrode head assembly and is provided with a circumferential groove 24, and with a cross bore 26. Groove 24 and cross core 26 are preferably filled with an implantable medical plastic 28 which may be either silicone rubber or polyurethane. A circular band of adhesive 30 surrounds plastic 28, and serves to seal the proximal end of plastic sleeve 16 and the distal end of an insulative sleeve 32 to the electrode head member 14.

Located within the proximal end of electrode head member 14 is a second bore 34, which receives the distal end of the coiled conductor 36. Coiled conductor 36 is electrically and mechanically coupled to electrode head member 14 by means of a crimping core 38, in conjunction with inwardly directed crimps 40 in head member 14. This mechanical connection mounts the conductor in fixed rotational relationship to the helix 10, allowing for transfer of torque to helix 10 via conductor 36. The distal end of crimping core 38 is provided with a slot 42 located at its proximal end, which engages the distal end of a screwdriver tipped stylet 44 in fixed rotational relationship. An elongated insulative sheath 46 is mounted between insulative sleeve 32 and head member 14, and extends proximally to the proximal end of the lead. Sheath 46 is preferably made of an implantable elastoplastic such as silicone rubber or polyurethane. In bipolar embodiments, a second, ring electrode may be located on the lead body, coupled to a second coiled conductor. These optional structures are not illustrated.

In use, the distal end of the lead illustrated in FIG. 1 is advanced through the venous system, the superior vena cava and through the tricuspid valve and rotated so that helix 10 pierces the endocardium and is screwed into the interior wall of the heart. While screwing helix 10 into the heart tissue, it is desirable that stylet 44 be engaged with the slot 42 in crimping core 38 and that the stylet and the lead body be rotated simultaneously, so that both structures work together to apply torque to the electrode head member 14 and thus to the helix 10.

Figure 2:
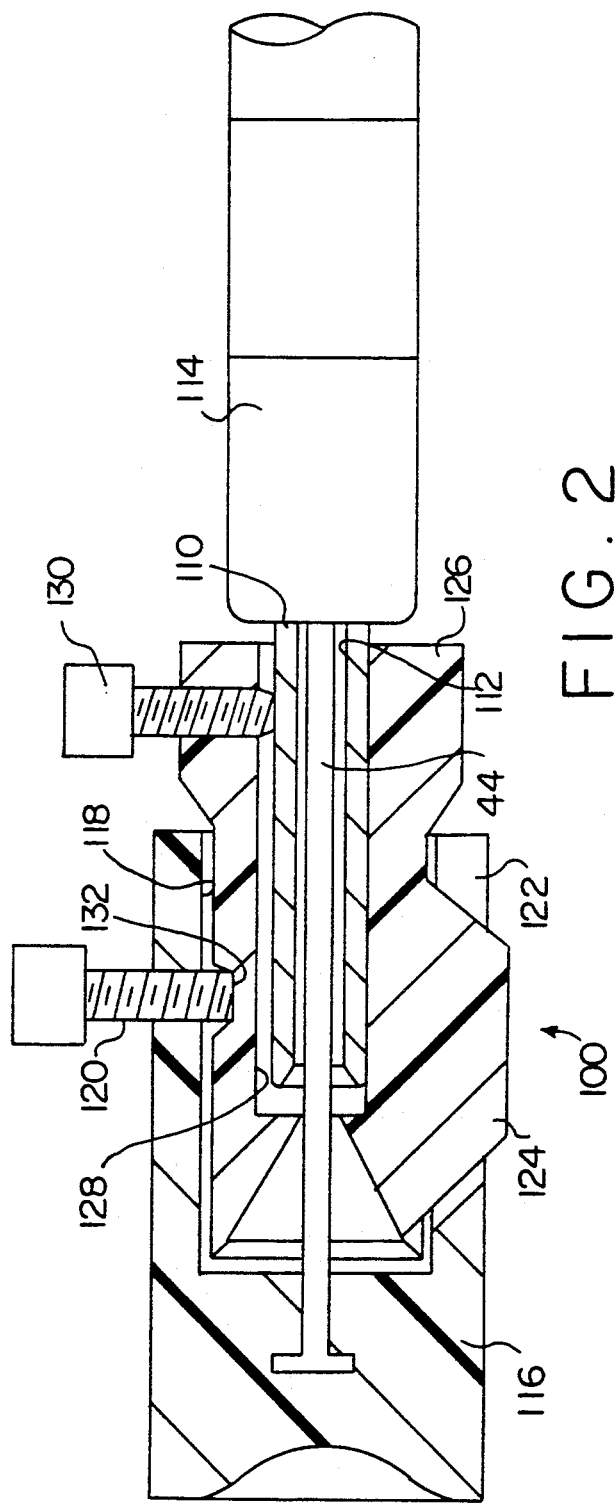
FIG. 2 is a side, cut away view of the proximal end of a pacing lead according to the present invention, with the stylet control fixture mounted thereto.

FIG. 2 illustrates a side cut away view of the connector assembly located at the proximal end of the lead illustrated in FIG. 1, along with the stylet control fixture 100, mounted thereto. Emerging from the proximal end of the pacing lead is a connector pin 110, which is provided with an internal bore 112, through which the proximal end of stylet 44 passes. Connector pin 110 is rigidly mechanically and electrically coupled to coiled conductor 36 (FIG. 1). This mechanical connection mounts conductor 36 in fixed rotational relationship to conductor 36 and allows torque applied to pin 110 to be transferred to helix 10 via conductor 36.

In bipolar embodiments, the proximal end of the pacing lead will typically be provided with a molded plastic sleeve 114, which may include a second electrical connector, not illustrated.

The proximal end of stylet 44 is embedded in a hollow, generally cylindrical outer knob member 116. Outer knob member 116 is provided with a distally facing internal lumen 118, and with a set screw 120. Outer knob 116 is also provided with a longitudinal slot 122, which receives a tab 124, located on an internal knob 126. Internal knob member 126 is also provided with a distally facing lumen 128 and a set screw 130.

In use, the internal knob member 126 is mounted over connector pin 110, and fastened thereto by means of set screw 130. Stylet 44 is then slid distally through connector pin 110 until the screwdriver shaped tip 45 at the distal end of stylet 44 engages slot 42 in crimping core 38. Typically, the length of stylet 44 is selected so that engagement of the tip of stylet 44 with crimping core 38 occurs when outer knob member 116 is located such that set screw 120 is proximal to the depression 132, with which it will engage. Outer knob member 116 is then slid distally, with projection 124 of inner knob member 126 engaging with slot 118, and set screw 120 is then tightened to engage with depression 132. This serves to stabilize the stylet longitudinally and rotationally with respect to connector pin 110, and therefore with respect to the coiled conductor 36 to which it is attached. Rotation of the outer knob member 116 thereafter thus causes simultaneous application of torque through stylet 44 and the conductor 36. Insulative sheath 46 also is fixedly located at both the proximal and distal ends of the lead and assists somewhat in transmission of torque.

The slight elongation of the lead body required in order to locate set screw 120 in depression 132 is also believed to assist in the transmission of torque, and serves to firmly locate the screwdriver tip 45 of stylet 44 in slot 42. Because the structure of the pacing lead (coil plus elastic sheath) is such that longitudinal elongation is possible, this causes no damage to the lead body, which will return to its original length after removal of stylet 44.

While the present invention is disclosed in the context of a pacing lead employing a fixed helix, it is believed that it may also be employed in the context of any lead employing an advanceable or rotatable helix of the type in which the fixation helix is rotationally fixed with regard to the distal end of the coiled conductor within the lead body. As such, the above embodiments should be considered exemplary, rather than limiting, in conjunction with the following claims.

In conjunction with the above description, we claim:

1. A medical electrode lead comprising:
    an elongated lead body comprising an elongated coiled conductor mounted within an elongated insulative sheath;
    an electrode head mounted to a distal end of said coiled conductor, and including a helical means for fixation of the electrode head adjacent body tissue to be stimulated, said helical fixation means mounted in fixed rotational relationship to said coiled conductor;
    a connector means mounted at a proximal end of said coiled conductor for coupling to said coiled conductor, mounted in fixed rotational relationship to said coiled conductor;
    a stylet insertable within said coiled conductor; and
    means for mounting said stylet in fixed rotational relationship to both said connector means and said helical fixation means.

2. A lead according to claim 1 wherein said elongated coiled conductor is mounted in fixed rotational relationship with said electrode head and with said elongated insulative sheath.

3. A lead according to claim 2 further comprising means for transferring torque from the proximal end of said elongated insulative sheath to said helix.

4. A lead according to claim 3 further comprising a stylet insertable within said elongated insulative sheath.

5. A lead according to claim 4 further comprising means for mounting said stylet in fixed rotational relationship to both said helix and said proximal end of said elongated insulative sheath.

6. A medical electrode lead comprising:
an elongated insulative sheath having a proximal and distal end;
an elongated conductor having a proximal end and a distal end and mounted within said elongated insulative sheath;
an electrode head mounted to the distal end of said conductor, and including a helical means for fixation of said electrode head adjacent body tissue to be stimulated, said helical fixation means mounted in fixed rotational relationship to said electrode head;
a connector assembly mounted to the proximal end of said elongated insulative sheath, and including an electrical connector coupled to the proximal end of said elongated conductor;
a stylet insertable within said elongated insulative sheath; and
means for mounting said stylet in fixed rotational relationship to both said connector assembly and said electrode head.

7. A lead according to claim 6 wherein said conductor comprises a coiled conductor and wherein said fixation means is mounted in fixed rotational relationship to said coiled conductor and wherein said connector assembly is mounted in fixed rotational relationship to said coiled conductor.

* * * * *